(12) United States Patent
Kasowski

(10) Patent No.: US 8,212,073 B2
(45) Date of Patent: Jul. 3, 2012

(54) PROTECTIVE BARRIER COMPOSITION COMPRISING REACTION OF PHOSPHOROUS ACID WITH AMINES APPLIED TO A SUBSTRATE

(76) Inventor: Robert Valentine Kasowski, West Chester, PA (US)

( * ) Notice: Subject to any disclaimer, the term of this patent is extended or adjusted under 35 U.S.C. 154(b) by 1130 days.

(21) Appl. No.: 10/579,642

(22) PCT Filed: Nov. 29, 2004

(86) PCT No.: PCT/EP2004/039836
§ 371 (c)(1),
(2), (4) Date: Nov. 3, 2008

(87) PCT Pub. No.: WO2005/054408
PCT Pub. Date: Jun. 16, 2005

(65) Prior Publication Data
US 2009/0048372 A1 Feb. 19, 2009

Related U.S. Application Data

(63) Continuation-in-part of application No. 10/497,129, filed as application No. PCT/US02/38855 on Dec. 5, 2002.

(60) Provisional application No. 60/393,674, filed on Jul. 3, 2002, provisional application No. 60/359,676, filed on Jan. 18, 2002, provisional application No. 60/340,476, filed on Dec. 7, 2001, provisional application No. 60/525,757, filed on Nov. 29, 2003, provisional application No. 60/554,094, filed on Mar. 18, 2004, provisional application No. 60/569,413, filed on May 7, 2004.

(51) Int. Cl.
*C07F 9/22* (2006.01)
*C07D 247/00* (2006.01)
*C09K 21/12* (2006.01)
*C08K 5/34* (2006.01)

(52) U.S. Cl. ............. 564/12; 564/14; 564/15; 544/214; 544/232; 568/14; 252/609; 524/86; 524/138; 524/148; 523/179

(58) Field of Classification Search .................. None
See application file for complete search history.

(56) References Cited

U.S. PATENT DOCUMENTS

| | | | |
|---|---|---|---|
| 4,369,064 A | 1/1983 | Von Bonin | |
| 4,599,375 A | 7/1986 | Berte et al. | |
| 4,992,481 A | 2/1991 | Von Bonin et al. | |
| 5,173,315 A | 12/1992 | Charlson et al. | |
| 5,948,837 A | 9/1999 | Cicchetti et al. | |
| 6,284,838 B1 | 9/2001 | Silbiger | |
| 6,730,381 B2 | 5/2004 | Horacek | |
| 7,115,677 B2 * | 10/2006 | Harashina et al. | 523/205 |
| 7,138,443 B2 * | 11/2006 | Kasowski et al. | 523/179 |
| 2002/0040083 A1 | 4/2002 | Kuwaki et al. | |
| 2005/0029499 A1 | 2/2005 | Kasowski et al. | |
| 2006/0074154 A1 * | 4/2006 | Harashina et al. | 524/115 |
| 2006/0175587 A1 * | 8/2006 | Kasowski | 252/601 |
| 2009/0054564 A1 * | 2/2009 | Eisentraeger et al. | 524/100 |

FOREIGN PATENT DOCUMENTS

| | | |
|---|---|---|
| JP | H03-35088 | 2/1991 |
| JP | 0507540 A | 3/1993 |
| JP | 2001303060 A | 10/2001 |
| WO | WO 01/77217 | 10/2001 |
| WO | WO-03/049812 A2 | 6/2003 |

OTHER PUBLICATIONS

Japanese Office Action dated Jan. 11, 2011, Japanese Application No. 2006-541478.

* cited by examiner

*Primary Examiner* — Joseph D Anthony

(57) ABSTRACT

This invention relates to flame barrier compositions as well as a method for the preparation of the flame barrier compositions formed from a flame retardant composition and water. A protective barrier comprises a flame barrier composition or a flame barrier polymer on top of a layer or sandwiched between two or more layers of glass, wood, paper, polymer films, and other layered materials as well as mixtures of layers.

8 Claims, No Drawings

PROTECTIVE BARRIER COMPOSITION COMPRISING REACTION OF PHOSPHOROUS ACID WITH AMINES APPLIED TO A SUBSTRATE

This application is a U.S. National Phase Application of PCT International Application PCT/US2004/039836, filed Nov. 29, 2004, which claims priority on U.S. Provisional Application Ser. No. 60/525,757, filed Nov. 29, 2003, U.S. Provisional Application Ser. No. 60/554,094, filed Mar. 18, 2004, U.S. Provisional Application Ser. No. 60/569,413, filed May 7, 2004; and a continuation-in-part of co-pending application Ser. No. 10/497,129, filed Sep. 20, 2004, incorporated herein by reference, which is the U.S. National Phase Application of PCT International Application PCT/US02/38855, filed Dec. 5, 2002, which claims priority on U.S. Provisional Application Ser. No. 60/393,674, filed Jul. 3, 2002, on Ser. No. U.S. Provisional Application 60/359,676, filed Jan. 18, 2002, and on U.S. Provisional Application Ser. No. 60/340,476, filed Dec. 7, 2001.

FIELD OF INVENTION

This invention relates to flame barrier compositions, flame barrier polymers, and protective barrier compositions and to their methods of preparation. It particular, this invention relates to flame barrier compositions deposited onto or between two or more substrates such as glass, wood, paper, polymeric films, and parts of structures such as a branch of a tree, a leaf, a building wall, a building roof, or a support beam.

BACKGROUND OF INVENTION

There is a need to have a flame barrier to protect people and/or property from fire. For example, the roof of a house could use a protective barrier if threatened by a fast moving forest fire. Limbs, leaves, or needles of trees need a flame barrier to stop the spread of a forest fire. The roof or walls of many modern buildings contain glass panels which may need a fire barrier to pass building fire code restrictions. The flame barrier may have to be transparent to be usable for architectural glass applications. Containers which come in a variety of shapes could also utilize a flame barrier built into the packaging to protect contents from fire. The parts and elements of many electronic and electrical devises have plastic parts that are required to have a certain level of flame resistance. In general terms, there is a need for a flame barrier that can be incorporated into the elements of any system that requires protection from heat or flames and there should be little environmental risk or human health risk exposure from the barrier.

Homes and businesses are being located near or within forests and are at risk from major fires. There is a need for a product that a home owner or fire department could spray onto trees, shrubs, and buildings to form a flame barrier as the danger of a fire approaches whether it is from a forest fire, neighboring structure, or adjoining structure. It would be further appealing if the product can be safely washed off after the danger passed. Such a product should pose little threat to the environment.

Currently, ammonium phosphates, ammonium polyphosphates, and ammonium sulfates are dissolved in water and sprayed or dropped onto forest fires. These materials do not form a film on the trees nor do they foam when subjected to heat or flames and thus do not form an insulating barrier on the trees. Such amine compounds are considered to pose little threat to the environment and are widely used even they do not appear to be very effective in preventing devastating fires. These compounds do not have very high thermal stability that occur in large forest fires.

Fire resistant glazings are one element of buildings that need to pass strict building codes for fire resistance. One such product is made by incorporating an inorganic silicate layer such as water glass and other ingredients sandwiched between two opposed panes of glass, which may be multiple layers. Such products under the trade names PYROSTOP® and PYRODUR® are sold by the Pilkington group of companies. This type of technology is discussed in GB 1585125 A. Incorporation of gels to control viscosity into such a construction is disclosed in U.S. Pat. No. 5,543,230. The inorganic silicate layer intumesces or foams when exposed to a flame or high heat. The foam protects because of its poor thermal conductivity and it also does not allow radiative transfer of heat. However, this glazing technology is very expensive and not highly automated. There is a need for a lower cost fire resistant glazing that is faster to make and less labor intensive.

Thus, there continues to be a need for an environmentally friendly alternative to halogenated polymers and halogenated flame retardants for molded plastic parts, with one use being in electronic and electrical equipment. The flame barrier polymer of this invention can be used for such applications.

SUMMARY OF INVENTION

This invention addresses such deficiencies of current products. This invention consists of transparent to non-transparent flame barrier compositions and flame barrier polymers. It also consists of protective barrier compositions. The active ingredient is an amine phosphate which does not appear to pose a threat to the environment. The flame barrier compositions are film formers that intumesce or foam when exposed to a flame or high heat and protects the side of the protective barrier not subject to the flame. The level of protection depends on factors such as the thickness of the barrier or the number of layers in the protective barrier composition. Such barriers would protect items stored in containers or contents of houses from a spreading fire or can be sprayed to form films that prevent fire spread.

This invention provides flame barrier, polymer barrier, and protective barrier compositions that give protection from heat and flames. This invention is a flame barrier composition comprising:

a) 99.9% to 0.5% by total weight of a flame retardant composition prepared by reacting an ethyleneamine or a mixture of ethyleneamines with polyphosphoric acid; and b) 0.1% to 99.5% water relative to total weight of composition.

This invention also comprises a flame barrier polymer comprising:

a) 30 to 99.75 percent by weight of a polymer or a mixture of polymers; and b) 0.25 to 70 percent by weight of the flame barrier composition.

In another aspect, the invention is a method for preparing a flame barrier composition, the method comprising the steps of:

a) reacting an ethyleneamine or a mixture of ethyleneamines with polyphosphoric acid and forming a two phase mixture comprising a viscous syrup that comprises the flame barrier composition, and a non-viscous phase;

b) separating the syrup from the non-viscous phase.

c) optionally, drying the syrup; and d) optionally, adding additional ethylenediamine or mixture of ethyleneamines to the syrup.

Preferably, the polyphosphoric acid has been prepared by ion exchange.

In yet another aspect, the invention is a flame barrier composition prepared by this method.

In yet another aspect, the invention is a protective barrier composition formed by deposition of the flame barrier composition or flame barrier polymer onto a substrate or between two or more substrates. A specific form of protective barrier composition is a fire resistant glazing assembly formed from at least two glass sheets having peripheral edges and spaced from each other to define an intermediate space, said sheets being connected together by a spacer along a peripheral region adjacent said peripheral edge and the flame barrier composition filling said intermediate space between the glass sheets. The glass sheets may be toughened glass. The glass sheets may be replaced by plastic sheets.

This invention also comprises methods of forming flame barrier compositions and protective barrier compositions and the products of these processes.

It was unexpected that the flame barrier compositions comprising a flame retardant composition and water would intumesce when heated or subjected to direct flame and that the foam would protect or insulate the other side from heat and flame for some period of time. It was unexpected that use of ion exchange prepared polyphosphoric acid would result in a syrup precipitate that when dried results in a flame retardant composition with superior stability than as otherwise obtained. It was also unexpected that the flame barrier composition can be flexible and transparent depending on composition. It was unexpected that the flame barrier composition, because of its resinous properties, would stick readily onto substrates onto which it was applied for a period of time and form a protective barrier.

DETAILED DESCRIPTION OF INVENTION

The synthesis of flame retardants using polyphosphoric acid is disclosed in PCT/US03/017268, and U.S. application Ser. No. 10/497,129 (PCT/US02/3885), filed May 28, 2004, the entire disclosure of which is incorporated herein by reference.

Unless the context indicates otherwise, in the specification and claims, the terms flame retardant composition, flame barrier composition, ethyleneamine, polymer, and similar terms also include mixtures of such materials. Unless otherwise specified, all percentages are percentages by weight and all temperatures are in degrees Centigrade (° C.).

The following terms are used herein:

A flame retardant composition is formed by the reaction of an acid with an ethyleneamine or a mixture of ethyleneamines.

A flame barrier composition is defined as an aqueous solution comprising the flame retardant composition. A flame retardant composition formed as an aqueous solution is a flame barrier composition. Water can be either added or removed from such a flame barrier composition. The flame barrier composition in its most general form is a mixture of (1) the reaction product of an ethyleneamine or a mixture of ethyleneamines with polyphosphoric acid, and (2) water. The water can be removed after construction to any desired level. The foaming can be reduced if the flame barrier composition contains too much water.

A flame barrier polymer is formed by melting a polymer and adding a flame retardant composition, which contains very little or no water.

A protective barrier composition is formed by deposition of a flame barrier composition or a flame barrier polymer onto or between substrates. The protective barrier composition comprises a substrate of arbitrary shape with the flame barrier composition deposited on it or between one or more substrates. The protective barrier composition can have multiple layers. The substrate is anything onto which the flame barrier composition or a flame barrier polymer is deposited. The substrate may be, for example, glass, glass-ceramic, metal, thermoplastic sheet, thermoset sheet, wood, and paper. It can be the branch of a tree, the roof of a building, complex interlayer of glass and flame barrier composition, or the wire of an electrical cable.

Ethyleneamines include compounds of the formula $H_2N$—$(CH_2)_2$—$(NH$—$(CH_2)_2)_n$—$NH_2$, in which n is an integer, preferably 0-5, as well as piperazine ($HN(CH_2CH_2)_2NH$) and its derivatives, such as aminoethylpiperazine. A review of ethyleneamines can be found in the *Encyclopedia of Chemical Technology*, Vol 8, pp. 74-108. Examples of ethyleneamines are ethylenediamine (EDA), diethylenetriamine (DETA), piperazine (PIP), triethylenetetramine (TETA), tetraethylenepentamine (TEPA), pentaethylenehexamine (PEHA), and aminoethylpiperazine.

Preparation of the Flame Retardant Composition

The flame retardant composition is formed by the reaction of an acid with an ethyleneamine or a mixture of ethyleneamines. Certain acids are difficult to obtain in very pure form. Polyphosphoric acid can be contaminated with orthophosphoric acid unless freshly prepared as this acid converts to orthophosphoric in aqueous medium, with the rate being dependent on many factors such as temperature, pH, and water content. Polyphosphoric acid can be prepared from the appropriate pure salt, such as sodium polyphosphate, using the acidic ion exchange resin: for example, AMBERLITE® 120H from Rohm and Haas, Philadelphia, Pa. An aqueous solution of, for example, the sodium salt is passed through an ion exchange column containing AMBERLITE® 120H, at which time almost all the sodium ions are removed leaving the pure acid. The acidity of the prepared acid will depend on the extent to which the sodium ions were removed. Thus not all the sodium must be removed to prepare the flame barrier compositions of the invention. The most preferred for strong acids is pH less than about 1.0.

Polyphosphoric acid, a commercially available form, can also be prepared by heating $H_3PO_4$ with sufficient phosphoric anhydride to give the resulting product, 82-85% $P_2O_5$ content, as described in the *Merck Index* 10$^{th}$ edition, #7453. Such a polyphosphoric acid can be obtained from Aldrich Chemical or Rhodia Corporation. Such commercial polyphosphoric acid contains some ortho-phosphoric acid, which is less desirable.

Ethyleneamines are often made from an industrial method based on ethylene and ammonia, according to *Encyclopedia of Chemical Technology*, Vol. 8, p. 82. A typical product distribution is EDA 55%, piperazine (PIP) 1.9%, DETA 23%, amino ethylpiperazine (AEP) 3.5%, TETA 9.9%, TEPA 3.9%, and higher ethyleneamines 2.3%. Other methods for synthesis of ethyleneamines also give similar distributions of the ethyleneamines. All the commercial methods synthesize all ethyleneamines at same time, thus requiring separation. The least expensive method to make one of the flame barrier compositions is to use this mixture of ethyleneamines directly or just the fraction with a boiling point greater or equal to that of EDA, for example. This will eliminate the costly step of separation and packaging of ethyleneamines into specific chemicals, which are then individually reacted with the acids and amines.

The most preferred is to use polyphosphoric acid obtained via ion exchange process to form the flame barrier compositions. Because polyphosphoric acid made via ion exchange contains a substantial amount of water, flame barrier compositions prepared with such acid contain substantial amounts of water. Such a flame barrier compositions separate into two phases on standing. The more dense phase is a viscous syrup, which is more thermally stable. The syrup made with ethyleneamine and polyphosphoric acid contains about 40%-50% water by weight, depending on the ethyleneamine used and the pH. The remaining portion is very dilute and non-viscous. The syrup enables a high concentrate aqueous amine phosphate solution.

The syrup made with DETA and polyphosphoric acid contains about 40% water and is quite viscous. This syrup is the most preferred flame barrier composition because it has very good thermal stability. The water content of syrup is dependent on the quality of the polyphosphoric acid as well. Because the syrup may contain nearly 80-90% of the theoretical yield, often only the syrup is used as the flame barrier composition and the remaining flame barrier composition, a dilute solution containing little flame retardant composition, is discarded. A further reason is that the dilute solution when dried is found to be less stable that dried syrup. Thus, the preferred manner to make flame barrier polymer is to use syrup dried to appropriate water content instead of drying the syrup and dilute solution together.

Following isolation of the syrup, additional ethylenediamine or mixture of ethyleneamines may be added to the syrup to further increase the pH and the amine content. The preferred ratio of acid to ethyleneamine is chosen so that the pH of the resultant flame barrier composition is less than about 7. Additional ethylenediamine or mixture of ethyleneamines may also be added to material prepared from commercial polyphosphoric acid and prepared, for example, as described in PCT/US03/017268, the disclosure of which is incorporated herein by reference. In either case, the preferred range is about 2.0 to 5.0, with about 3.0 to 3.5 being most preferred.

It would be expected that less pure polyphosphoric acid, which contains smaller chain polyphosphoric and phosphoric acids, would be acceptable for many applications, and for reasons such as cost and easier to make. One of the advantages of flame barrier composition prepared with commercial polyphosphoric acid is it is less expensive to manufacture and cost is an important consideration. Commercial polyphosphoric acid contains some phosphoric acid contaminant according to the manufacturer, which could account for lower thermal stability compared to ion exchange prepared flame barrier composition. Polyphosphoric acid prepared with ion exchange may have very little phosphoric acid contaminant, because the sodium polyphosphate is thought to contain practically no sodium phosphate. The manufacturer indicates the chain length is about 12. Thus, the molecular weight of syrup is very high, which accounts for resinous behavior of syrup.

The polyphosphoric acid content should be such that at least 90% by weight if the polyphosphoric acid has chain length n greater than or equal to 3. A polyphosphoric acid with at least 95% chain length greater than or equal 3 is preferred. A polyphosphoric acid with at least 99% chain length greater than or equal 3 is more preferred. Polyphosphoric acid prepared by ion exchange is most preferred. It is also most preferred to use sodium polyphosphate with average chain length greater 10 for ion exchange process.

Such ethyleneamine/polyphosphoric acid flame barrier compositions form resins that are very flexible if they contain some water. The resins become quite brittle if the water is completely removed. The intumescent behavior is still maintained even if the resin does not contain water. Addition of amine compounds such as melamine, melamine phosphate, dimelamine phosphate, melamine polyphosphate, melamine pyrophosphate (MPP), and mixtures thereof with the ethyleneamine/polyphosphoric acid/water flame barrier resin composition may improve barrier properties. Another part of the composition can be to add an anti drip agent at a loading of 0.1 to 1%, with 0.25 to 0.5% most preferred. For some compositions, it may be preferred to use a flame barrier composition made with the higher molecular weight ethyleneamines such as TEPA.

The flame barrier compositions made with polyphosphoric acid were resinous in behavior. Compositions from EDA and phosphoric acid or pyrophosphoric acid made in an aqueous medium form a crumb or a powdery type material on removal of water and not a resinous product. A combination of polyphosphoric acid with either phosphoric acid and or pyrophosphoric acid reacted with ethyleneamines can be resinous and is part of this invention.

Syrup was only formed when an ethyleneamine such as EDA, DETA, TETA, and PEHA were reacted with ion exchanged polyphosphoric acid. The syrup did not form when commercial polyphosphoric acid was reacted with an ethyleneamine. Syrup also does not reform. For example, dry the syrup to form a flame retardant composition. Re-dissolve the flame retardant composition in water and the syrup phase does not separate.

Syrup with concentration greater than 45% by weight of flame retardant composition is particularly useful because when sprayed onto a substrate as it does not drip off. The syrup was found to still protect the wooden rod from burning with a torch even after the rod had been allowed to stand vertically for two weeks. A syrup with low viscosity will drip off easily. Thus, it is preferred to have a concentration of the syrup of at least 45%. It is also particularly useful that the syrup not be too acidic or too basic so as not to damage the substrate to which it is applied. The preferred pH is 1.75 to 7.0. It is also particularly useful for the polyphosphoric acid to be made with high molecular weight sodium polyphosphate. High molecular weight leads to higher yield of syrup. It is preferred that the sodium polyphosphate have a average chain length of at least 10.

Flame Barrier Composition

The preferred practice is to form the resinous flame barrier composition from the flame retardant composition formed by the reaction of an ethyleneamine such as EDA, DETA, TETA, or mixtures thereof with polyphosphoric acid. Such reactions are carried out in water. Water in the flame barrier composition allows the material to be sprayed for deposition, to stick to the substrate as a continuous film, and also to be transparent and flexible. The flame barrier composition could also be deposited by forcing through a die if the viscosity is high. Those knowledgeable in the field would have a variety of methods. The amount of water is chosen so that the flame barrier composition has the desired viscosity. The water can be removed after the flame barrier composition is formed to any level including complete removal. Complete removal of water would result in a flame retardant composition with a little color but still transparent if thin enough.

Flame barrier compositions made with commercial polyphosphoric acid are made by dissolving the polyphosphoric acid in some water and then adding ethyleneamine. Such composition can be quite viscous and water can be added if it is necessary to lower the viscosity. Such a flame barrier composition is completely soluble in water and can form continuous film on or between substrates. No syrup precipitant is formed with this procedure.

Other ingredients may be added to the barrier compositions: for example, pigments are added for color. Various compounds such as fumed silica thicken the flame barrier composition. Addition of compounds such as melamine pyrophosphate improve the foaming behavior but require sub micron particle if transparency is important.

These flame barrier compositions have some of the desirable properties of polymers such as resinous films forming naturally. The best practice is to remove the water to the desired amount which depends on the application or to even add water. It may be necessary to add water for applications requiring low viscosity. Water can be removed either from the flame barrier composition at synthesis or it could removed even entirely from the protective barrier composition after deposition. The flame barrier composition is quite stable and can be heated with or without vacuum to remove water. Heating with a stream of air could also extract moisture.

It is possible to add flame retardants to the flame barrier composition. For example ammonium phosphates (with one or two hydrogen atoms), ammonium polyphosphate, and ammonium sulfate. Such flame retardants could dissolve in the flame barrier composition if the water content is sufficient.

Other additives are water glass or a gel that cross links with heat. It may be necessary to remove some or all of the water from the flame barrier composition after the film is made. Heating in air or heating with vacuum would remove water and an air draft would speed up the process. Gels are often constructed from epoxides of ethylene oxide and/or propylene oxide and primary and/or secondary, aliphatic, aromatic and/or aliphatic mono- and/or polyamines. It is also possible to use panes of plastic as a single or multi-layer substrate, for example, polymethyl methacrylate, polyvinyl chloride, polycarbonate, cellulose esters, aromatic esters, or polyurethane.

Flame Barrier Polymers

Flame barrier polymers can be formed by adding the flame retardant composition to a polymer. The best practice is to dry the syrup so that it contains less than 1% water. The last 1% of water content is high temperature water content that comes off at rather high temperature and which adds considerable cost. For lower melt temperature polymers, it may not be necessary to remove all the water. Extruders with vacuum capability can remove small amounts of water as well. Because of the high thermal stability, a variety of drying methods are acceptable to dry the syrup to the desired water content. The preferred is a Littleford rotary vacuum dryer. Some reduction in pH can occur in drying. One can add an ethyleneamine to the flame retardant composition in the Littleford dryer to raise pH to a less acidic or higher value.

The flame barrier polymer or the flame barrier composition may contain other additives such as other flame retardants and re-enforcing agents, a partial list being chopped glass, aramid fibers, talc, mica, nano-clay, or clay. Since flame retardants work by different mechanisms, a combination of our flame barrier composition with other flame retardants may perform more efficiently. Other additives include such ingredients as stabilizers, release agents, flow agents, dispersants, plasticizers, anti-drip agents, and pigments. Other additives can include colorants, thickeners, corrosion inhibitors, stabilizers, and bactericides. Practitioners in the field of flame retardance are knowledgeable in the selection of these ingredients which add functionality. To improve electrical properties, compounds such as zinc borate (such as FIREBRAKE® 500 by US Borax Corp.) or barium meta-borate (Buckman Corp., Nashville, Tenn.) can be added to flame barrier polymer composition. Magnesium hydroxide by itself requires a high loading and processes poorly. A flame barrier polymer which include magnesium hydroxide would process much better because of lubricant properties of the flame retardant composition. Among the phosphorus compounds that can be used in a formulation with the compositions of this invention are the bis(diaryl phosphate) esters of dihydroxyaromatic compounds, as illustrated by resorcinol bis(diphenyl phosphate), hydroquinone bis(diphenyl phosphate), and bisphenol A bis (diphenyl phosphate).

Items made with the flame barrier polymers of this invention may require a surface sealant. A paint adhesion promoter for plastics such as BOND AID® or similar product available in retail paint stores can be used to coat the item and even add a second surface coating for more complete sealing of the surface.

The flame barrier compositions of the flame barrier polymers can be applied to structural components such as beams or rafters for all applications. The structural component would be protected by the flame barrier from weakening due to heat or fire. Examples are beams made of wood, plastic, metal, or even plywood.

A complete description of glass and ceramic glass is given in *Kirk-Othmer Encyclopedia of Chemical Technology* (ECT), 4th Ed., Vol. 12. Glasses are primarily silicate glasses with various amounts of $Al_2O_3$, $B_2O_3$, $LiO_2$, $Na_2O$, $K_2O$, CaO, BaO, PbO, ZnO and even other ingredients, which are discussed in Vol. 12 of ECT. Glass-ceramics are polycrystalline materials formed by controlled crystallization of glass. The kind of glass or ceramic is not limited to those described in ECT, Vol. 7. Soda lime glass is often used in windows.

The flame barrier compositions and flame barrier polymers contain an amine phosphate. Amine phosphate flame retardants are well known and studied and type of chemistry is thought to pose little harm to the environment. Our compositions should pose little harm to the environment.

Nearly all polymers are suitable for use with this invention. The classes of polymers to which the invention are applicable include the following: acrylic, butyl, cellulosics, epoxy, furan, melamine, neoprene, nitrile, nitrocellulose, phenolic, polyamide, polyester, polyether, polyolefin, polysulfide, polyurethane, polyvinyl butyral, silicone, styrene-butadiene, butyl rubber, polyethylene naphthalate, and vinyl.

Polymer and polymer compositions to which the compositions of the invention are applicable to include the following:

1. Mono and diolefins such as polypropylene(PP), thermoplastic olefins (TPO), polyisobutylene, polymethylpentene, polyisoprene, polybutadiene, polyethylene with or without crosslinking, high density polyethylene, low density polyethylene, or mixtures of these polymers. Copolymers of mono and diolefins including other vinyl monomers such as ethylene-propylene copolymers, ethylene-vinyl acetate copolymers. Terpolymers of ethylene with propylene and a diene such as hexadiene, cyclopentadiene or ethylidiene norborene and vinyl monomers such as vinyl acetate. Mixtures of polymers under 1.

2. Polystyrene, poly p methyl styrene, poly α methylstyrene, and copolymers of styrene or α methylstyrene with dienes or acryl derivatives such as styrene-butadiene, styrene-actrylonitrile, styrene-alkylmethylacrylate, styrene-butadiene-alkylacrylate, styrene-maleic anhydride, and styrene-acrylonitrile-methylacrylate, syndiotactic polystyrene, high impact polystyrene (HIPS), acrylonitrile butadiene styrene (ABS).

3. Polyphenylene oxide and polyphenylene sulfide and their mixtures with styrene polymers or with polyamides.

4. Polyurethane's derived from polyethers, polyesters and polybutadiene with terminal hydroxyl groups on one hand and aliphatic or aromatic polyisocyanates on the other as well as their precursors.

5. Polyamides and copolymers derived from diamines and dicarboxylic acids and/or from aminocarboxylic acids or the corresponding lactams, such as polyamide 4, polyamide 6, polyamide 6/6, 6/10, 6/12, 4/6, 66/6, 6/66, polyamide 11, polyamide 12, aromatic polyamides based on aromatic diamine and adipic acid: and iso- and/or terephthalic acid and optionally an elastomer as modifier, for example poly-2,4-trimethyl hexamethylene terephthalamide, poly m phenylene-isophthalamide.

6. Polyesters derived from dicarboxylic acids and dialcohols and/or from hydrocarboxylic acids or the corresponding lactones such as polyethylene terephthalate (PET), polybutylene terephthalate (PBT), polyethylene terephthalate/polybutylene terephthalate mixtures, polyethylene terephthalate/polybutylene terephthalate copolymers, poly 1,4-dimethyl cyclohexane terephthalate, polyhydroxybenzoates, and co-polymers with ethylene.

7. Polyvinyl chloride and copolymers with ethylene, copolymers of tetra fluro ethylene and ethylene.

8. Thermoset polymers include for example unsaturated polyester resins, saturated polyesters, alkyd resins, amino resins, phenol resins, epoxy resins, diallyl phthalate resins, as well as polyacrylates and polyethers containing one or more of these polymers and a crosslinking agent. A review of thermosets is found in Ullmann's *Encyclopedia of Industrial Chemistry*, Vol A26, and p 665.

9. Polymers for insulation such as fluorinated ethylene-propylene (FEP), cross linked polyethylene (XLPE), ethylene-propylene rubber (EPR), tree cross linked polyethylene (TRXLPE), and ethylene vinyl acetate (EVA).

10. Cellulose acetate, flexible polyurethane, rigid polyurethane.

11. Fluoropolymers and co-polymers such as TEFZEL®, DuPont Co, Wilmington, Del. Elastomers such as SPANDEX® as defined in *Encyclopedia of Chemical Technology*, Polyimides such as KAPTON®, DuPont Co., Wilmington, Del. And defined in *Encyclopedia of Chemical Technology*.

12. Ethylene vinyl acetate, ethylene methyl, ethyl, and butyl acrylate ethylene (methyl, ethyl, butyl) acrylate, ethylene n butyl acrylate glycidyl methacrylate, -ethylene vinyl acetate carbon monoxide, ethylene n butyl acrylate carbon monoxide, vinyltrimethylsilane, or vinyltriethylsilane ethylene methyl acrylate, ethylene methyl acrylate, ethylene acrylic and methacrylic acid, ethylene acrylic and methacrylic acid ionomers (Zn, Na, Li, Mg), maleic anhydride grafted polymers.

Polymers such as polycarbonate (PC) (also known as bisphenol A carbonate), polyphenylene oxide (PPO), polyphenylene sulfide are less flammable than polymers such as nylon 6, PBT, PET, and ABS. Thus alloys such acrylic/PC, ABS/PC, HIPS/PPO, nylon 6/PPO, PBT/PPO, and PET/PPO will require less of the flame retardant composition to obtain the desired level of flame retardance. PC based polymer barrier composition will be particularly attractive for fire resistant assemblies. In one embodiment, the flame barrier polymer comprises 20 to 95 wt % of a polymer selected from the group consisting of polycarbonate, polyphenylene oxide, polyphenylene sulfide, and mixtures thereof; 20 to 95 wt % of a polymer selected from the group consisting of nylon 6, polybutylene terephthalate, polyethylene terephthalate, acrylic polymers, ABS, high impact polystyrene, and mixtures thereof; and 0.5 to 20 wt % of the flame barrier composition.

INDUSTRIAL APPLICABILITY

The flame barrier compositions can be sprayed onto trees by aerial equipment or from the ground by spray equipment to form protective barrier on the leaves and branches. The flame barrier compositions can be sprayed onto structures or trees or shrubs that are burning to contain the fire. A protective coating on the unburned part of the structure would retard spreading of the fire. For example, spraying could create a fire line to contain a forest fire or protect a structure. The flame barrier compositions can be used in fire extinguishers or in sprinkler systems, a much more effective way of controlling a fire than water.

The flame barrier compositions or flame barrier polymers can be applied between glass plates or polymeric plates to form a transparent window, wall, fire resistant glazing, or other building component for architectural use. Such a structure can be several layers of alternating glass plates or polymeric plates and barrier layers. The structure could include polymer films with or without flame retardation to make safety glass that does not shatter. When one side is subjected to heat, the barrier will intumesce and form a nontransparent barrier to shield the other side from the heat. The degree of protection will determine the number of layers. One can also use multiple layers of flame retarded polymeric sheet separated by flame barrier composition with glass sheets on the exterior. Similar multi layer structures can be used in transportation as in ships, airplanes, spacecraft, and railcars. Another name is fire resistant glazing panel which is defined in U.S. Pat. No. 6,159,606 as comprising at least two glass sheets between which is placed a transparent material that provides protection from a flame on the other side.

The flame barrier polymer can be used to make molded parts used in applications such as insulation on wires and cable jackets. The flame barrier polymer can be used to replace applications now served by halogen containing polymers and polymers containing chlorinated or brominated compounds, for example, engineering polymers, fibers, and films.

It is also possible to place the flame barrier composition or flame barrier polymer between polymer films which can be rolled and then unrolled when used. This sandwich structure can then be placed between two substrates such two glass plates with a process similar to that used for making safety glass and laminates. Such a structure may need to be processed at increased temperature, for example 150° C. to get proper adhesion of the components. The polymeric films can contain a flame retardant such as the flame retardant composition of this invention to further improve the flame barrier protection.

The flame barrier composition can also be used as a replacement for water glass now used in making certain types of architectural glass. For example, PYROSTOP® made by Pilkington Co. which consists of a series of float glass layers separated by water glass layers could use the flame barrier composition.

A thickening agent can be added to the composition so that the foam that formed during a fire would be more rigid. U.S. Pat. No. 5,766,770 teaches that it would be advantageous to introduce a minimum of 5% by weight of sub-microscopic particles of an inorganic compound or a metallo-organic compound of silicon, aluminum, titanium or zirconium into the intumescent layer in order to increase the viscosity thereof on foaming. Fumed silica has been shown to work for this invention.

The advantageous properties of this invention can be observed by reference to the following examples, which illustrate but do not limit the invention.

EXAMPLES

Sources of Materials

Melamine was obtained from DSM Corp., Saddlebrook, N.J. PCS Inc., Newark, N.J. for 85% concentration phosphoric acid. Polyphosphoric acid, sodium acid pyrophosphate, sodium polyphosphoric acid, were obtained from Aldrich Chemical, Milwaukee, Wis. Polyphosphoric acid also obtained from Rhodia Corporation, St. Louis, Mo. DETA, TETA, TEPA, and EDA were obtained from Huntsman, Houston, Tex. FR150 anti drip agent from Shamrock Technology, Newark, N.J. Very fine ion exchange resin from Purolite, Philadelphia, Pa. BOND AID® from W. M. Barr & Co., Memphis, Tenn. Littleford Day Company, Florence, Ky. PUROLITE® ion exchange resin, Purolite, Philadelphia, Pa.

Example 1

This example illustrates the preparation of a flame barrier composition:

Polyphosphoric acid is quite expensive compared to sodium polyphosphate, available from Tilley Chemical Corp., Baltimore, Md., USA. Polyphosphoric acid can be made by dissolving sodium polyphosphate in water and then extracting the sodium ions with an ion-exchange resin (AMBERLITE® 120 from Aldrich Chemical) to form polyphosphoric acid.

The flame barrier composition demonstrates feasibility for barrier formation. First, 2640 g of sodium polyphosphate was dissolved in 15.4 L of water. The solution was processed through an ion exchange column to obtain polyphosphoric acid. The DETA/polyphosphoric acid flame barrier composition was prepared by adding diethylenetriamine (DETA) to the polyphosphoric acid solution until a pH of about 3.25 was reached. Syrup, which separates to the bottom, was separated from the rest of the reaction mixture. The syrup was about 35% water and 65% flame retardant composition. The syrup shows substantial intumescense when heated with a propane torch.

A wooden rod 1 cm (⅜ inch) in diameter and 46 cm (18 inches) in length was obtained. One end was coated with the syrup to about 10.1 cm (4 inches). The coating was done by simply dipping a finger into the syrup and spreading it on the end to coat about 10.1 cm (4 inches) of one end. The rod was allowed to lie horizontally above the ground for 30 minutes so that access would drip off. The coating was much less than 0.16 cm (1/16 inch) in thickness. A propane torch, used to solder copper pipes, from Ace Hardware with a 2.54 cm (1 inch) flame was now used to test the flame retardance. The torch was applied to the uncoated end of the rod with a sweeping motion back and forth over about 6.4 cm (2.5 inches) of one end for one minute. The uncoated end of the rod catches on fire and burns during application. After removal, the flame continues for a while then goes out but the rod smolders and the end disintegrates after about 20 minutes. Now the same procedure was applied to the coated end using the identical propane torch which had not been changed. After one minute, there was only a slight burning which immediately went out after removal. A black char had formed on the surface of the rod that the flame was applied. The back side of the rod looked substantially protected and was not blackened. The backside coating was a little yellow but still transparent. It was apparent that the coating had protected the rod from igniting from such an intense and focused heat source. This example demonstrates that the flame barrier composition forms a protective barrier.

Example 1a

This Example shows the preparation of a flame barrier polymer:

The syrup of Example 1 was dried with a Littleford rotary vacuum. The dried syrup (PNS) along with melamine pyrophosphate (MPP) was then mixed into polymers with a Banbary mixer at a weight percent loading compared to weight of composition. Bars were molded at 0.16 cm (1/16 inch) thickness. All samples contained 0.5% FR150 anti-drip agent. The bars were burned in a manner similar to UL94 test, except that the samples were not aged. The bars were all flexible indicating good elongation, a key mechanical property for molded parts. Table I summarizes the results.

TABLE I

Summary of properties of flame barrier polymers.

| Polyethylene | 63.5% PNS | 24% MPP | 12% UL94 rating V0 |
| Polypropylene | 69.5% PNS | 20% MPP | 10% UL94 rating V0 |
| Engage 8480 | 63.5% PNS | 24% MPP | 12% UL 94 rating V0 |
| Nylon 6 | 69.5% PNS | 20% MPP | 10% UL94 rating V0 |

Example 2

This example illustrates a flame barrier composition:

The procedure of Example 1 was repeated except that ethylenediamine (EDA) was added so that the pH of the solution was about 3.4. Similar results were found when the syrup was applied to the end of a 1.0 cm (⅜ inch) thick wooden rod. The propane caused one end to burn rapidly when exposed to the propane torch for one minute. The end coated with the syrup of this example did not burn. A char formed that protected the interior of the stick.

Examples 3-4

This example illustrates a flame barrier compositions prepared using commercial polyphosphoric acid:

These examples were prepared with DETA and commercial polyphosphoric acid from Rhodia, St. Louis, Mo., USA. First, 250 g of polyphosphoric acid were placed in each of two separate aluminum pans. Next, 170 g of DETA and 145 g of water were mixed together and then added to pan #1. To pan #2, 130 g of DETA and 130 g of water were added. Each pan was mixed slowly with a wooden rod to enable the reactions to go to completion in both pans. Some DETA escapes due to substantial heat release. Two resinous products were obtained. The resinous products showed protective behavior when applied to the ⅜ inch thick wooden rod and exposed to propane torch for one minute.

Example 5

This example illustrates a flame barrier composition with melamine and commercial polyphosphoric acid:

In this example, a mixture of melamine polyphosphate with the TETA salt of polyphosphoric acid was prepared. First, 3 g of melamine was added to 15 g of water and heated to about 80° C. About 18 g of polyphosphoric acid was added and reacted for about 15 minutes at which time some melamine polyphosphate has been made which appears as a white particulate. Then, TETA was added to bring the mixture to pH of about 3.5. The melamine part of the composition precipitates into the syrup and is collected with the syrup. Excellent intumescense is observed with such a combination.

Example 6

This example illustrates a flame barrier composition prepared with an amine that is not an ethyleneamine:

In this example, diaminocyclohexane salt of polyphosphoric acid was prepared. About 18 g of polyphosphoric acid (prepared via ion exchange) was placed in a glass container. Then, diaminocyclohexane was added to bring the pH to about 3.5. Then, the mixture was partially dried in a vacuum oven.

Example 7

This example illustrates preparation of flame barrier composition with commercial polyphosphoric acid:

First, 260 g of commercial polyphosphoric acid from Rhodia is dissolved in approximately 500 ml of water. Then approximately 130 g of DETA is added. Some DETA is lost due to foaming as the reaction is very intense. The 1.0 cm (⅜ inch) stick was dipped into the flame barrier composition. The dipped end was submitted to a propane torch as in Example 1. Much charring and intumescense occurs which protects the interior of the stick. The stick does not burn and the results are similar to Example 1. A second batch was made using 390 g of polyphosphoric acid, 750 g of water and 195 g of DETA. The burn results were very similar for the 1.0 cm (⅜ inch) rod.

Examples 8-12

This example illustrates the investigation of properties of the syrup:

Sodium polyphosphate (33 g) was dissolved in 141 g of water. The ion exchange column contained very fine PUROLITE® ion exchange resin in hydrogen form. The sodium polyphosphate solution was run through the IX column to obtain polyphosphoric acid. The acid was placed in a column. Various ethyleneamines were added and mixed. Various ethyleneamines were then added and mixed. The results are shown in Table II. The amount of ethyleneamine is labeled amt ea. The amount of syrup extracted (about 30 ml) is similar but with EDA being the least. Purposely the pH was varied. A pH of at least 2 is needed to get most of the syrup. Important to mix the solution very well or else the ea will remain mostly with the solution, not the syrup. The yield of syrup is 29-30 ml. The amount of solution varies depending on when collection of polyphosphoric acid began or ended from the ion exchange column. The viscosity of the syrup is lowest for EDA and highest for TEPA.

TABLE II

| | | Syrup formed from ion exchange polyphosphoric acid and ethyleneamine (EA). | | | | | |
|---|---|---|---|---|---|---|---|
| EA | amt EA | syrup | pH soln | pH syrup | ml soln | wt. syrup | viscosity |
| 8 DETA | 10.5 g | 30 ml | 5.1 | | 400 | 46.4 g | medium |
| 9 DETA | 9.6 g | 30 ml | 4.7 | 2.9 | 370 | 48.3 g | medium |
| 10 DETA | 10 g | 30 ml | 5.8 | 5.1 | 550 | 52.6 g | medium |
| 11 TEPA | 11 g | 29 ml | 3.1 | 2.0 | 360 | 44.9 g | very high |
| 12 EDA | 8 g | 29 ml | 3.3 | 3.1 | 375 | | lowest |

Example 13

This example illustrates the thermal stability of the flame retardant composition.

The syrup from Example 8 and the compound from Example 7 were dried in a vacuum oven for 30 minutes at 200° C. The weight loss for the syrup from Example 8 was found to be less than that of the compound from Example 7, showing that the syrup from Example 8 has much more utility for making flame barrier polymers.

Example 14

This example illustrates the thermal stability of the flame retardant composition.

The syrup from Example 8 and a sample of ammonium phosphate were each dried in a conventional oven for 30 minutes at 260° C. The weight loss for the syrup from Example 8 was found to be much less than ammonium phosphate, showing that the syrup from Example 8 has much more thermal stability. Leaves and branches coated with the syrup from Example 8 should be more fully protected in a fire.

Example 15

This example illustrates a protective barrier composition:

Two pieces of regular window glass (Ace Hardware) were cut into squares 7.6 cm (3 inches) on a side. One piece was coated with the syrup from Example 8. A propane torch applied to the glass piece with no coating causes the glass to break in about 3-5 seconds. The same propane torch similarly applied to the glass with the syrup exposed to the torch does not break for 10 minutes. Thus, the syrup is a very effective flame barrier composition and should be useful for window glazings.

Example 16

Syrup was only formed when an ethyleneamine such as EDA, DETA, TETA, and PEHA were reacted with ion exchanged polyphosphoric acid. The syrup did not form when commercial polyphosphoric acid was reacted with an ethyleneamine. Syrup also does not reform. For example, dry the syrup to form a flame retardant composition. Re-dissolve the flame retardant composition in water and the syrup phase does not separate.

Syrup with concentration greater than 45% by weight of flame retardant composition is particularly useful because when sprayed onto a substrate as it does not drip off. The syrup was found to still protect the wooden rod from burning with a torch even after the rod had been allowed to stand vertically for two weeks. A syrup with low viscosity will drip off easily. Thus, it is preferred to have a concentration of the syrup of at least 45%. It is also particularly useful that the syrup not be too acidic or too basic so as not to damage the substrate to which it is applied. The preferred pH is 1.75 to 7.0. It is also particularly useful for the polyphosphoric acid to be made with high molecular weight sodium polyphosphate. High molecular weight leads to higher yield of syrup. It is preferred that the sodium polyphosphate have a average chain length of at least 10.

Example 17

The syrup and solution formed in the reaction mixture of Example 1 are each dried. Thermal Gravimetric Analysis (TGA) shows a weight loss of at least 10% at 300° C. for the dried dilute solution and less than 1% weight loss for the dried syrup. The large difference in stability is attributed to the dilute solution containing lower molecular weight product. The dried syrup appears to be resinous. The dried dilute solution appears to be a mixture of particles and resin. The particles are low molecular weight material.

Example 18

The temperatures of the barrels and die of a twin screw extruder are set at 250° C., as is appropriate for processing nylon 6. The first sample consists of 70% nylon pellets, 10% MPP, and 20% dried syrup from Example 1a. The composition is compounded with no problem in the extruder. The second sample consists of 70% nylon pellets, 10% melamine pyrophosphate (MPP), and 20% dried dilute solution from Example 1. The sample compounds very poorly in the extruder. The polymer looks degraded as it is more brittle. A third run is done with the material obtained by drying the syrup and dilute solution together. The polymer is of intermediate quality further showing the superiority of the dried syrup. This result is consistent with lower thermal stability of the dried dilute solution compared to syrup as shown in Example 17.

Example 19

Ion exchange polyphosphoric acid is used to prepare syrups with pH of 3.7 and 4.5. The syrups are dried in a rotary vacuum dryer. The pH of a 10% solution of the dried syrup is about 3 for each sample, as some of the ethyleneamine is removed in drying. A third run on the rotary vacuum dryer is made. After the drying is completed, DETA is added to the melt and mixed for 5 min without vacuum. The product is then extracted and cooled. The pH is then close to the starting pH of 4.5. This method permits formation of compositions that are not stable under the long drying conditions of the rotary vacuum dryer.

Having described the invention, we now claim the following and their equivalents.

What is claimed is:

1. A method for preparing a flame retardant composition, the method comprising the steps of:
   a) reacting an ethyleneamine or a mixture of ethyleneamines with polyphosphoric acid and forming a two phase mixture comprising a viscous syrup that comprises the flame retardant composition, and a non-viscous phase; and
   b) separating the syrup from the non-viscous phase; with the proviso that said polyphosphoric acid reactant has been prepared by ion exchange.

2. The method of claim 1 in which the ethyleneamine or a mixture of ethyleneamines is selected from the group consisting of ethylenediamine, diethylenetriamine, piperazine, triethylenetetramine, tetraethylenepentamine, pentaethylenehexamine, aminoethylpiperazine, and mixtures thereof.

3. The method of claim 2 in which the ethyleneamine is a mixture of ethyleneamines.

4. The method of claim 1 in which the syrup has a pH of 1.7 to 7.0.

5. The method of claim 1 additionally comprising, after step b):
   c) drying the syrup and forming a dried syrup.

6. The method of claim 5 in which the dried syrup, dried to a water content of less than 0.5%, has a weight loss of less than 1.5% at 315° C. in a TGA run at 20° C. per minute in nitrogen.

7. The method of claim 5 additionally comprising, after step c),
   d) the step of adding an ethyleneamine or a mixture of ethyleneamines to the dried syrup.

8. The method of claim 1 in which the polyphosphoric acid is prepared from sodium polyphosphate that has an average chain length of at least 10.

* * * * *